United States Patent [19]
Mori et al.

[11] Patent Number: 5,972,525
[45] Date of Patent: Oct. 26, 1999

[54] SOLID PARTICLE CONTAINING ACTIVE CARBON, SUPPORT AND CATALYST

[75] Inventors: Kenji Mori, Niigata; Takeshi Koyama, Yokohama; Koji Takiguchi, Handa; Susumu Fujii; Hiroshi Fujishima, both of Kitakyushu, all of Japan

[73] Assignees: JGC Corporation; Catalysts & Chemicals Industries Co., Ltd., both of Japan

[21] Appl. No.: 08/879,132

[22] Filed: Jun. 19, 1997

[30] Foreign Application Priority Data

Jun. 20, 1996 [JP] Japan ..................... 8-160000

[51] Int. Cl.$^6$ ......................................................... B32B 5/16
[52] U.S. Cl. ......................... 428/632; 428/402; 428/403; 428/404; 428/633; 428/634; 502/182; 502/413
[58] Field of Search ..................... 428/402, 403, 428/404, 633, 634, 632; 502/417, 242, 239, 182, 202, 208, 238, 263, 350, 355, 413, 415

[56] References Cited

U.S. PATENT DOCUMENTS

| | | | |
|---|---|---|---|
| 3,855,185 | 12/1974 | Loveless et al. | 260/80.78 |
| 3,932,306 | 1/1976 | Rona | 252/430 |
| 4,078,011 | 3/1978 | Glockner et al. | 260/677 |
| 4,560,817 | 12/1985 | Bobsein et al. | 585/273 |
| 4,629,767 | 12/1986 | Shyr et al. | 525/339 |

FOREIGN PATENT DOCUMENTS

| | | |
|---|---|---|
| 54-85194 | 7/1979 | Japan . |
| 63-503460 | 12/1988 | Japan . |
| 3193616 | 8/1991 | Japan . |
| 4089458 | 3/1992 | Japan . |
| 4154611 | 5/1992 | Japan . |
| 6239795 | 8/1994 | Japan . |
| WO 87 07601 | 12/1987 | WIPO . |

OTHER PUBLICATIONS

"Measurement of Fluidization Characteristics in Vinyl Acetate Synthesis Reactor", Toshio Kawaguchi, Hiroshi Kimura, and Toshihisa Wakasugi; Sekiyu Gakkaishi, vol., 29, No. 2, 1986, pp. 168–173.

*Primary Examiner*—Hoa T. Le
*Attorney, Agent, or Firm*—Webb Ziesenheim Logsdon Orkin & Hanson, P.C.

[57] ABSTRACT

Solid particles which comprise a substantially homogeneous mixture of an active carbon and an attrition-resistant inorganic substance and which have an average particle size of smaller than 300 $\mu$m. The average particle size is preferred to range from 20 to 200 $\mu$m. The inorganic substance is, for example, silica, titania, zirconia, alumina or silica-alumina. The active carbon is preferred to be contained in an amount of 5 to 70% by weight. The solid particles can be produced by spray drying a slurry containing an active carbon or a precursor thereof and an attrition-resistant inorganic substance or a precursor thereof so that particles having an average particle size of smaller than 300 $\mu$m are obtained, and calcining the particles. The inorganic substance or precursor thereof is preferably present in a colloidal or hydrogel state in the slurry. The particles are excellent in attrition resistance and mechanical strength.

A catalyst support and a catalyst comprising the solid particles are also disclosed.

18 Claims, No Drawings

SOLID PARTICLE CONTAINING ACTIVE CARBON, SUPPORT AND CATALYST

FIELD OF THE INVENTION

The present invention relates to solid particles containing active carbon having an average particle size of smaller than 300 μm which are excellent in attrition resistance and mechanical strength and a process for producing the particles. The present invention also relates to a catalyst support and a catalyst comprising the solid particles.

BACKGROUND OF THE INVENTION

The active carbon is used in a wide variety of processes as an adsorbent, a catalyst, a support or the like. That is, the active carbon is widely used not only as a catalyst but also as a support which carries thereon a catalytic component for reactions such as the ortho-para hydrogen conversion, the halogenation or dehalogenation or the oxidation.

A large number of catalysts comprising an active carbon as a support are known, which include catalysts for vinyl acetate production, halogenation or dehalogenation, oxidation reduction and olefin polymerization. Specifically, for example, a catalyst comprising zinc acetate supported on an active carbon has been used for the production of vinyl acetate from acetylene and acetic acid (Sekiyu Gakkaishi (Journal of Petroleum Institute of Japan), Vol. 29, No. 2, (1986)). Further, various catalysts have been proposed for the vapor phase reaction of oxygen, carbon monoxide and an alcohol to produce a carbonic acid diester, which include a catalyst prepared from an active carbon impregnated with a metal halide or a mixed metal halide (Published Japanese Translation of PCT Patent Applications from Other States, No. 503460/1988) and a catalyst comprising a catalytic component such as copper chloride supported on active carbon obtained from a vegetable or polymer raw material (Japanese Patent Laid-open Publication No. 6(1994)-239795). Further a catalyst comprising a platinum group metal chloride and for example a bismuth compound supported on active carbon has been proposed to be used for the vapor-phase catalytic reaction of carbon monoxide and an alkyl nitrite to produce a carbonic acid diester (Japanese Patent Laid-open Publication No. 4(1992)-89458).

The above reactions are generally exothermic. It is preferred that the exothermic vapor-phase reaction is conducted in the fluidized bed reactor capable of effectively removing heat. Even when the reaction proceeds endothermically, the fluidized bed reactor is preferred because of its effective heat transfer. For efficiently carrying out the reaction in the fluidized bed reactor, it is preferred to use a granular catalyst which is excellent in not only catalytic activity but also mechanical strength and attrition resistance and which has a controlled particle size and uniform bulk density. Especially, a granular catalyst having a controlled small particle size may enable attainment of more efficient heat transfer, a well-controlled reaction conditions and easy scale up of the vapor-phase fluidized bed reactor.

However, the active carbon (granular active carbon) is brittle and is easily attrited, so that, it has been desired for the granulated active carbon used as a catalyst for the fluidized bed or a catalyst support to be improved in the mechanical strength and attrition resistance.

Further, the granulated active carbon obtained by conventional methods generally has a relatively large particle size, and it has been difficult to prepare a granulated active carbon whose particle size is less than 300 μm.

Proposals have also been made for active carbon supports having improved attrition resistance and mechanical strength. For example, Japanese Patent Laid-open Publication Nos. 3(1991)-193616 and 4(1992)-154611 disclose granulated active carbons of high strength which are obtained by milling active carbon powder, bentonite clay and a phosphorus compound or boron compound in specified proportions and granulating followed by calcination. However, the granulated active carbons obtained by the methods of the above publications have a size of, for example, about 4.5 mm in diameter and 6 mm in length and even after pulverization, have a size of about 0.59 to 2.38 mm. Thus, any granulated active carbon having a particle size which is suitable for a catalyst for fluidized bed has not been obtained.

Japanese Patent Laid-open Publication No. 54(1979)-85194 discloses an attrition-resistant active carbon support (or active carbon catalyst) produced by impregnating an attrition-resistant support material with an aqueous solution of saccharide, drying and pyrolyzing the saccharide in the absence of air to carbonaceous substance to thereby cover the surface of the support material with active carbon. This publication reports that when $SiO_2$ or $Al_2O_3$ of 35 to 130 μm in average particle size obtained by spray drying is used as a support material, solid particles covered with active carbon having the same average particle size are obtained.

The inventors have made extensive and intensive studies with respect to active carbon which is excellent in attrition resistance and which has a small particle size for fluidized bed. As a result, it has been found that a process, comprising spray drying a slurry containing an active carbon or a precursor thereof and an attrition-resistant inorganic substance or a precursor thereof so as to obtain particles having an average size of smaller than 300 μm; and calcining the particles, can provide solid particles which comprise a substantially homogeneous mixture of the active carbon and the attrition-resistant inorganic substance, which have an average particle size of smaller than 300 μm and which are excellent in mechanical strength and attrition resistance.

OBJECT OF THE INVENTION

An object of the present invention is to provide solid particles containing active carbon having an average particle size of smaller than 300 μm, which are excellent in attrition resistance and mechanical strength, and a process for producing the particles. Another object of the present invention is to provide a support and a catalyst, each of which comprises the above solid particles and is. suitable for the fluidized bed reactor.

SUMMARY OF THE INVENTION

The solid particles of the present invention comprise a substantially homogeneous mixture of an active carbon and an attrition-resistant inorganic substance and have an average particle size of smaller than 300 μm.

It is preferred that the average particle size of the solid particles range from 20 to 200 μm.

The attrition-resistant inorganic substance is at least one metal oxide selected from silica, titania, zirconia, alumina and silica-alumina.

The solid particles of the present invention are preferred to contain the active carbon in an amount of 5 to 70% by weight, especially 5 to 50% by weight.

In the present invention, it is preferred that the solid particles have a pore volume of 0.1 to 1.0 ml/g as measured by an $N_2$ adsorption method and mercury porosimetry. Further, it is preferred that the solid particles have the above pore volume and simultaneously a specific surface area of 100 to 1200 m²/g.

The solid particles of the present invention are preferred to further comprise phosphorus and/or boron in an amount of 2 to 10% by weight as its oxide.

The solid particles of the present invention can be produced by a process comprising the steps of:
spray drying a slurry containing an active carbon or a precursor thereof and an attrition-resistant inorganic substance or a precursor thereof so that particles having an average particle size of smaller than 300 μm are obtained, and
calcining the particles.

The attrition-resistant inorganic substance is at least one metal oxide selected from silica, titania, zirconia, alumina and silica-alumina.

In the process of the present invention, the particles can contain a phosphorus compound and/or a boron compound prior to calcination of the particles.

In the process for producing the solid particles, the solids in the slurry can be subjected to a wet pulverizing or dispersing operation prior to the spray drying. It is preferred that the calcination of the particles is conducted at 400 to 800° C. in an atmosphere of inert gas.

The solid particles of the invention which comprise a substantially homogeneous mixture of an active carbon and an attrition-resistant inorganic substance and which have an average particle size of smaller than 300 μm are suitably used as a support or a catalyst.

Moreover, the present invention provides a catalyst comprising the above solid particles and a catalytic component supported thereon. This catalyst is useful for producing a carbonic acid diester or vinyl acetate.

The catalyst for producing a carbonic acid diester includes for example those which comprise the solid particles and, supported thereon, a salt containing a metal and a halide as the catalytic component. In this catalyst for producing a carbonic acid diester, the catalytic component comprises
(i) a metal halide and (ii) an alkali metal compound and/or alkaline earth metal compound,
(i) a metal halide and (iii) a tertiary organo-phosphorus compound having an aryl and/or alkyl group, or
(i) a metal halide and (iv) an inorganic carbonate.

DETAILED DESCRIPTION OF THE INVENTION

First, the solid particles containing active carbon of the present invention will be described in detail below.

The solid particles of the present invention comprise a substantially homogeneous mixture of an active carbon and an attrition-resistant inorganic substance.

In the solid particles, which can be produced by the process described below in more detail, the active carbon and the inorganic substance are mixed substantially homogeneously not only on the surface thereof but also in the bulk thereof. That is, the active carbon is homogeneously dispersed in the hard inorganic substance, so that the solid particles can exhibit excellent attrition resistance and mechanical strength.

It should be noted in this regard that the support disclosed in the Japanese Patent Laid-open Publication No. 54(1979)-85194 cited hereinbefore has a structure in which the active carbon merely covers the surface of the support material, as different from the structure of the invention in which the active carbon and the inorganic substance are substantially homogeneously mixed as described above.

This difference in the structure should produce a difference in the effect.

For example, when solid particles are used in a fluidized bed reactor, the surface of the particles generally wears away with the time of use. In the case where the support described in the above publication is used, the support particles collide with each other to wear away and lose the active carbon which is present only on the surface thereof. The loss of the active carbon on the surface results in loss of desired effect as a support or catalyst.

By contrast, the solid particles of the present invention can be used effectively for a prolonged period of time because the active carbon is substantially homogeneously dispersed in the inorganic substance not only on the surface thereof but also in the bulk thereof.

The solid particles of the present invention have an average size of smaller than 300 μm, preferably from 20 to 200 μm and especially from 30 to 100 μm.

The attrition-resistant inorganic substance as a constituent of the solid particles is a metal oxide selected from among silica, titania, zirconia, alumina and silica-alumina. The attrition-resistant inorganic substance may also be a mixture of these.

The solid particles are preferred to contain the active carbon in an amount of 5 to 70% by weight, more preferably 5 to 60% by weight, especially 5 to 50% by weight and still especially 5 to 40% by weight.

The properties such as attrition resistance of the solid particles can be further improved by incorporating the phosphorus compound and/or boron compound together with the above metal oxide.

Examples of suitable phosphorus compounds include phosphoric acid and ammonium hydrogenphosphate, and examples of suitable boron compounds include boric acid. It is preferred that phosphorus and/or boron is contained in the solid particles in an amount of 2 to 10% by weight as an oxide thereof.

The solid particles of the present invention are preferred to have a pore volume of 0.1 to 1.0 ml/g as measured by an $N_2$ adsorption method and mercury porosimetry and are also preferred to have a specific surface area of 100 to 1200 m²/g as measured by BET (Brunauer, Emmett and Teller, see K. S. W. King, Characterization of Catalysts, p1, 1980 and ASTM D366-78) method.

The terminology "pore volume" used herein means the volume of pores having a size of smaller than 1 μm.

The solid particles of the present invention can be produced by a process comprising the steps of:
spray drying a slurry containing an active carbon or a precursor thereof and an attrition-resistant inorganic substance or a precursor thereof so that particles having an average size of smaller than 300 μm are obtained, if desired applying wet pulverizer of the slurry so that the active carbon or precursor thereof is pulverized to 30 μm or less prior to the spray drying, and
calcining the particles.

In the preparation of the slurry, various common active carbons can be used as a raw material, examples of which include active carbons prepared from wood, coconut husk, sawdust, lignin, coal, petroleum pitch, phenol resin and epoxy resin.

It is preferred that active carbon powder whose average size generally ranges from about 0.05 to 150 μm, especially from about 0.1 to 100 μm is used as the raw material.

In the present invention, the slurry can also be prepared using a precursor convertible to active carbon by calcination, for example wood, coconut husk or sawdust or saccharides.

In the preparation of the slurry, the above metal oxide such as silica, titania, zirconia, alumina or silica-alumina is used as the attrition-resistant inorganic substance. This inorganic substance is preferred to have an average particle size of 0.005 to 10 μm, especially 0.005 to 3 μm.

Further, the slurry can be prepared using a precursor convertible to the above metal oxide by calcination, for example aluminum hydroxide or titanium hydroxide.

Of the above inorganic substances or precursors thereof, those which are in the form of colloidal or hydrogel in the slurry are preferred. Especially, colloidal particulates are preferred because of their high adhesion. Specifically, silica sol and alumina hydrogel can suitably be used as the slurry.

A solvent such as water or an alcohol can be used in the preparation of the slurry containing the active carbon or precursor thereof and the inorganic substance or precursor thereof.

The total weight of the active carbon or precursor thereof and the inorganic substance or precursor thereof contained in the slurry is preferred to range from 10 to 40% by weight.

In the preparation of the slurry containing the active carbon or precursor thereof and the inorganic substance or precursor thereof according to the present invention, it is preferred that the active carbon or precursor thereof is added to the slurry of inorganic substance or the sol of precursor thereof, for example silica sol, and then mixed.

It is preferred that the slurry containing the active carbon or precursor thereof and the attrition-resistant inorganic substance or precursor thereof is well agitated and subjected to pulverization or homogenization by means of a wet pulverizer such as a sand mill, a pearl mill or an attritor so that the components are mixed together to form a substantially homogeneous dispersion.

In the present invention, the slurry as prepared above is then spray dried to provide particles whose average size is smaller than 300 μm, preferably 20 to 200 μm and still preferably 30 to 100 μm.

The spray drying can be performed by conventional methods.

In the present invention, the thus obtained particles are calcined. The properties such as attrition resistance of the final particles can be improved by incorporating in the particles the above phosphorus compound and/or boron compound prior to the calcination. The incorporation of the phosphorus compound and/or boron compound in the particles can be carried out for example either by adding the phosphorus compound and/or boron compound to the slurry containing the active carbon or precursor thereof and the attrition-resistant inorganic substance or precursor thereof or by impregnating the particles, obtained by the spray drying of the above slurry, with a solution containing the phosphorus compound and/or boron compound.

The resultant solid particles are calcined at 400 to 800° C., preferably 500 to 700° C. in an atmosphere of inert gas such as nitrogen or argon whose oxygen content is lower than 0.5 mol %, thereby obtaining the desired solid particles.

The solid particles provided by the present invention have an average size of smaller than 300 μm and are excellent in attrition resistance and mechanical strength.

These solid particles are useful as, for example, an adsorbent, a support or a catalyst.

When used as a support or a catalyst in fluidized bed reactors, the solid particles of the present invention are preferred to have the following physical properties:

(1) specific surface area (measured by BET method) which is preferred to range from 100 to 1200 $m^2/g$, especially from 200 to 1000 $m^2/g$;

(2) pore volume (measured by the $N_2$ adsorption method and mercury porosimetry) which is preferred to range from 0.1 to 1.0 ml/g, especially from 0.2 to 0.8 ml/g;

(3) bulk density (measured by the graduated cylinder method) which is preferred to range from 0.4 to 1.3 g/ml, especially from 0.5 to 1.1 g/ml;

(4) attrition resistance which is preferred to range from 0 to 10% by weight per 15 hr, especially from 0 to 7% by weight per 15 hr, wherein the attrition resistance is measured by fluidization of the solid particles in accordance with ACC method (as described in the specification of U.K. Patent No. 737,429) and represents the proportion of attrition which occurs during 15 hr from the 5th hr to the 20th hr both from the initiation of fluidization; and (5) average particle size (measured by the micromesh sieve method) which is preferred to range from 20 to 200 μm, especially from 30 to 100 μm.

With respect to the support or catalyst for fluidized bed reactor, the properties such as attrition resistance and average particle size are important factors for maintaining stable fluidization. In particular, the attrition resistance is an important factor in the industrial fluidized bed reactor. It is desired that these factors are within the above ranges.

The solid particles of the present invention are especially suitable for use as support catalysts using the particles as the support will be described below.

Examples of such catalysts include those for carbonic acid diester production or for vinyl acetate production.

The above catalyst for carbonic acid diester production is a catalyst for oxidative carbonylation which is carried out in the vapor-phase by reaction of oxygen, carbon monoxide and an alcohol. This catalyst for oxidative carbonylation is one comprising the support of the solid particles containing active carbon and, supported thereon, a catalytic component such as a salt containing a metal and a halogen, for example a metal halide or a mixed metal halide. Of the metal halides, a copper halide is preferably used. Another example of this catalyst is a catalyst in which the catalytic component supported on the solid particles comprises (i) a metal halide and (ii) an alkali metal compound and/or alkaline earth metal compound, (i) a metal halide and (iii) a tertiary organo-phosphorus compound-having an aryl and/or alkyl group, or (i) a metal halide and (iv) an inorganic carbonate.

The catalyst for carbonic acid diester production is also a catalyst which is used in the vapor-phase catalytic reaction of carbon monoxide and an alkyl nitrite. This catalyst is for example one comprising the solid particles containing active carbon and, supported thereon, catalytic components of a chloride of platinum group metal and a compound of at least one metal selected from iron, copper, bismuth, cobalt, nickel and tin.

The catalyst for vinyl acetate production is a catalyst which is used in the addition of acetic acid to acetylene. This catalyst is, for example one comprising the solid particles containing active carbon and, supported thereon, zinc acetate.

Moreover, the present invention provides various hydrogenation catalysts. Examples of these include a catalyst for hydrogenation of unsaturated aldehyde to produce a saturated aldehyde or an unsaturated alcohol, which catalyst comprises the solid particles and, supported thereon, a catalytic component of a noble metal such as Os or Ir; a catalyst for hydrogenation of an aliphatic nitrile compound to an amine, which catalyst comprises solid particles and, supported thereon, a noble metal such as Rh, Pt or Pd; catalysts for hydrogenation of an aromatic compound, for example, a catalyst for hydrogenation of o-xylene to 1,2-dimethylcyclohexene, which catalyst comprises the solid particles and, supported thereon, a noble metal such as Ru, Rh, Pt or Pd, and a catalyst for hydrogenation of benzene to cyclohexene, which catalyst comprises the solid particles and, supported thereon, Ru; catalysts for hydrogenation of a polycyclic compound, for example a catalyst for hydrogenation of biphenyl to cyclohexylbenzene or bicyclohexyl, which catalyst comprises the solid particles and, supported thereon, a noble metal such as Rh, Ir, Ru, Pt or Pd; catalysts for hydrogenation of a condensed ring compound, for example a catalyst for hydrogenation of naphthalene to decalin, which catalyst comprises the solid particles and, supported thereon, a noble metal such as Ru, Rh, Pt or Pd.

Of these catalysts, the catalyst for carbonic acid diester production and the catalyst for vinyl acetate production are especially preferred.

These catalysts can be prepared by supporting the catalytic component on the solid particles according to conventional methods. The preparation of the especially preferred catalyst for carbonic acid diester production which comprises the support of the solid particles and, supported thereon, a metal halide (i) such as copper halide and any of an alkali metal compound and/or an alkaline earth metal compound (ii) such as an alkali metal hydroxide and/or an alkaline earth metal hydroxide, a metal halide (i) and a tertiary organophosphorus compound having an aryl and/or alkyl group (iii), and a metal halide (i) and an inorganic carbonate (iv) will be described in detail below.

The copper halide (i) is, for example a halide of monovalent or divalent metal, such as copper chloride, copper bromide, copper iodide or copper fluoride. These can be used in combination. Cupric halides are preferred, and cupric chloride is especially preferred.

The alkali metal hydroxide and/or alkaline earth metal hydroxide (ii) may be selected from among alkali metal hydroxides such as lithium hydroxide, sodium hydroxide and potassium hydroxide and alkaline earth metal hydroxides such as barium hydroxide and calcium hydroxide. These can be used in combination.

The tertiary organophosphorus compound having an aryl and/or alkyl group (iii) may be selected from among triaryl phosphines such as triphenylphosphine, triarylphosphites such as triphenyl phosphite, alkylarylphosphines such as dimethylphenylphosphine, trialkyl phosphites such as trimethyl phosphite and triethyl phosphite and trialkyl phosphates such as trimethyl phosphate and triethyl phosphate. These can be used in combination.

The inorganic carbonate (iv) is, for example a single salt having one cation such as $K_2CO_3$, $Na_2CO_3$, $CaCO_3$ or $BaCO_3$, a salt having two cations such as $KNaCO_3$ or $KHCO_3$ and an inorganic carbonate having a polyatomic ion such as $(NH_4)_2CO_3$. These can be used in combination.

In the present invention, it is preferred that the catalyst for carbonic acid diester production is produced by supporting on the solid particles the copper halide (i) together with the alkali metal hydroxide and/or alkaline earth metal hydroxide (ii), the copper halide (i) together with the tertiary organophosphorus compound having aryl and/or alkyl groups (iii) or the copper halide (i) together with the inorganic carbonate (iv).

In the preparation of the catalyst, the component (i) together with the component (ii), the component (i) together with the component (iii) or the component (i) together with the component (iv) as they are or in the form of a solution obtained by dissolving them in an appropriate solvent is contacted with the solid particles so that the catalytic components concerned are supported on the solid particles. When the catalytic components are used in the form of a solution, for example the copper halide (i) is used in the form of a solution in ethanol, methanol, water or the like; the alkali metal hydroxide or alkaline earth metal hydroxide (ii) is used in the form of an aqueous solution; the tertiary organophosphorus compound having an aryl and/or alkyl group (iii) is used in the form of a solution in an alcohol or the like; and the inorganic carbonate (iv) is used in the form of a solution in water or the like.

When the catalytic components are supported on the solid particles, this can be accomplished either by first supporting on the solid particles one catalytic component and thereafter the other component or by supporting on solid particles both catalytic components simultaneously. Further, it is also possible to support the catalytic components on the solid particles by using a previously prepared solution containing all the catalytic components.

After being brought into contact with the solutions of the catalytic components, the solid particles are preferably treated in an air atmosphere or a flowing inert gas (for example, nitrogen, argon or helium) at an appropriate temperature.

Further, the catalytic components can be supported on the solid particles by an appropriate method selected from among the impregnation method, the milling method, the coprecipitation method and the like.

Although the amount of catalytic components supported on the solid particles are not particularly limited in the preparation of the catalyst of the invention as long as the obtained catalyst can exhibit an activity in the synthetic reaction of a carbonic acid diester, the following amounts of the catalytic components are preferred. When the component (i) together with the component (ii) or the component (i) together with the component (iv) are supported on the solid particles, the copper halide (i) is preferably supported in an amount of about 1 to 20% by weight, still preferably about 2 to 15% by weight in terms of Cu/(copper halide+ solid particles). It is preferred that the alkali metal hydroxide or alkaline earth metal hydroxide (ii) is supported on the solid particles in an amount of 0.3 to 2, especially 0.5 to 1.5 in terms of the molar ratio of hydroxyl group (OH)/Cu based on the Cu atoms of the copper halide (i).

The inorganic carbonate (iv) is preferred to be supported in an amount of 0.2 to 1.3, especially 0.4 to 0.8 in terms of the carbonate group ($CO_3$ group) of the inorganic carbonate, namely, the molar ratio of $CO_3$ group/Cu atom of the copper halide.

When the catalyst components of the copper halide (i) and the tertiary organophosphorus compound having an aryl and/or alkyl group (iii) are supported on the solid particles, a method other than mentioned above can also be employed in which a copper complex is synthesized from the components (i) and (iii) before supported on the solid particles (method described in International Application Publication WO 90/15791).

With respect to the amount of components (i) and (iii) supported on the solid particles, it is preferred that the copper halide (i) is supported in an amount of 2 to 10% by weight in terms of the ratio of Cu of the copper halide to the solid particles (Cu/solid particles) and that the tertiary organophosphorus compound having an aryl and/or alkyl group (iii) is supported in a molar ratio to Cu atom of the copper halide (i) of 0.05 to 0.4.

When a copper complex is first synthesized from the components (i) and (iii) and then supported on the solid particles, it is preferred that the copper complex is supported in an amount of 2 to 10% by weight in terms of the ratio of Cu of the copper complex to the carrier (Cu/solid particles).

The above catalyst of the present invention can catalyze the reaction of an alcohol with carbon monoxide and oxygen to produce a carbonic acid diester with high activity.

Although the above catalyst of the present invention can be used in a fixed bed reactor, a fluidized bed reactor and other types of reactors without any particular limitation, it is especially useful for a fluidized bed reactor.

EFFECT OF THE INVENTION

The solid particles of the present invention comprise a substantially homogeneous mixture of active carbon and inorganic substance as described above. The solid particles are excellent in attrition resistance and mechanical strength and have an average particle size as small as less than 300 $\mu$m.

These attrition-resistant solid particles containing active carbon are especially useful as a catalyst support.

For example, a catalyst for vapor-phase reactor carried out in a fluidized bed reactor formed by using the solid particles of the present invention enables an efficient heat transfer and therefore enables efficient removal of the heat of reaction in, for example the oxidative carbonylation of an alcohol for producing a carbonic acid diester, so that the scale up of the vapor-phase fluidized bed reactor can easily be established.

EXAMPLE

The present invention will now be illustrated in greater detail with reference to the following Examples, which in no way limit the scope of the invention.

In the following Examples, the cupric chloride solution was prepared by dissolving 25.0 g of cupric chloride in 100 ml of distilled water, and the sodium hydroxide solution was prepared by dissolving 22.3 g of sodium hydroxide in 100 ml of distilled water.

Example 1

Production of Solid Particles (Support)

200 g of active carbon powder prepared from coconut husk was mixed well with 4000 g of silica sol of 20% by weight in concentration (Cataloid s-20LE having an average particle size of 16 $\mu$m, produced by Catalysts & Chemicals Industries Co., Ltd.) and pulverized by a wet pulverizer attritor (manufactured by Miike Seisakusho) so as to cause the active carbon powder to have a particle size of 2.5 $\mu$m. Subsequently, the mixture was spray dried to obtain fine spherical particles having an average size of 60 $\mu$m. The fine spherical particles were calcined at 500° C. in flowing nitrogen to obtain solid particles (a) having an average size of 60 $\mu$m. The morphology of the particles (support) (a) was observed under a microscope with the result that the formation of desirable spherical particles was confirmed. The properties thereof are given in Table 1.

Production of Catalyst

The thus obtained solid particles were impregnated with the cupric chloride solution in an amount of 6% by weight in terms of Cu and dried. Thereafter, the obtained solid particles were impregnated with the sodium hydroxide solution so as to cause the molar ratio of OH/Cu to be 1.3 and dried. Thus, catalyst (A) was obtained. The properties of the catalyst (A) are given in Table 2.

Test of Attrition Resistance of Support and Catalyst (by ACC Method)

45 g of the thus obtained particles (support) (a) or catalyst (A) was charged in a stainless steel pipe of 40 mm in inside diameter having a gas distributor at a lower part thereof. The support or catalyst was fluidized for 20 hr by passing air at room temperature through the distributor at a rate of 7 Nl/min. The proportion of attrition which occurred during 15 hr from the 5th hour to the 20th hour was measured. The results are given in Tables 1 and 2.

Test of Catalyst Activity

Dimethyl carbonate (DMC) was synthesized with the use of the above obtained catalyst (A).

1 ml of the catalyst (A) was charged in a stainless steel pipe of 8 mm in inside diameter, which was used as a high-pressure fixed bed reactor. Then, methanol, carbon monoxide and oxygen were introduced in the reactor at respective rates of 5 g/hr, 14 Nl/hr and 0.35 Nl/hr and reaction was carried out under conditions such that the pressure was 8 kg/cm$^2$G and the temperature was 130° C. to produce DMC.

The performance of the catalyst at 2 hr from the initiation of the reaction is given in Table 2.

Example 2

Production of Solid Particles (Support)

50 g of active carbon powder prepared from coconut husk was mixed well with 4750 g of silica sol of 20% by weight in concentration (Cataloid S-20LE produced by Catalysts & Chemicals Industries Co., Ltd.) and pulverized by a wet pulverizer attritor so as to cause the active carbon powder to have a particle size of 2.4 $\mu$m. Subsequently, the mixture was spray dried to obtain fine spherical particles having an average particle size of 60 $\mu$m. The fine spherical particles were calcined at 500° C. in flowing nitrogen to obtain solid particles (b) having an average size of 60 $\mu$m. The properties of the particles (support) (b) are given in Table 1.

Production of Catalyst

The thus obtained solid particles were impregnated with the cupric chloride solution in an amount of 6% by weight in terms of Cu and dried. Thereafter, the obtained solid particles were impregnated with the sodium hydroxide solution so as to cause the molar ratio of OH/Cu to be 1.3 and dried. Thus, catalyst (B) was obtained.

The obtained support and catalyst were subjected to the same attrition resistance test and catalyst activity test as in Example 1. The results are given in Tables 1 and 2.

Example 3

Production of Solid Particles (Support)

100 g of active carbon powder prepared from sawdust was mixed well with 4500 g of silica sol of 20% by weight in concentration (Cataloid S-20LE produced by Catalysts & Chemicals Industries Co., Ltd.) and pulverized by a wet pulverizer attritor. Subsequently, spray drying was performed, thereby fine spherical particles having an average size of 70 $\mu$m were obtained. The fine spherical particles were calcined at 500° C. in flowing nitrogen to obtain solid particles (c) having an average size of 70 $\mu$m. The properties of the particles (support) (c) are given in Table 1.

Production of Catalyst

The thus obtained solid particles were impregnated with the cupric chloride solution in an amount of 10% by weight in terms of Cu and dried. Thereafter, the obtained solid particles were impregnated with the sodium hydroxide solution so as to cause the molar ratio of OH/Cu to be 1.5 and dried. Thus, catalyst (C) was obtained.

The obtained support and catalyst were subjected to the same attrition resistance test and catalyst activity test as in Example 1. The results are given in Tables 1 and 2.

Example 4

Production of Solid Particles (Support)

300 g of active carbon powder prepared from coal was mixed well with 3500 g of silica sol of 20% by weight in concentration (Cataloid S-20LE produced by Catalysts & Chemicals Industries Co., Ltd.) and pulverized by a wet pulverizer attritor so as to cause the active carbon powder to have a particle size of 2.0 μm. Subsequently, the mixture was spray dried to obtain fine spherical particles having an average particle size of 60 μm. The fine spherical particles were calcined at 500° C. in flowing nitrogen to obtain solid particles (d) having an average particle size of 60 μm. The properties of the particles (support) (d) are given in Table 1.

Production of Catalyst

The thus obtained solid particles were impregnated with the cupric chloride solution in an amount of 10% by weight in terms of Cu and dried. Thereafter, the obtained solid particles were impregnated with the sodium hydroxide solution so as to cause the molar ratio of OH/Cu to be 1.3 and dried. Thus, catalyst (D) was obtained.

The obtained support and catalyst were subjected to the same attrition resistance test and catalyst activity test as in Example 1. The results are given in Tables 1 and 2.

Example 5

Production of Solid Particles (Support)

500 g of active carbon powder prepared from petroleum pitch was mixed well with 2500 g of silica sol of 20% by weight in concentration (Cataloid S-20LE produced by Catalysts & Chemicals Industries Co., Ltd.) and pulverized. Subsequently, the mixture was spray dried to obtain fine spherical particles having an average size of 70 μm. The fine spherical particles were calcined at 600° C in flowing nitrogen to obtain solid particles (e) having an average size of 70 μm. The properties of the particles (support) (e) are given in Table 1.

Production of Catalyst

The thus obtained solid particles were impregnated with the cupric chloride solution in an amount of 10% by weight in terms of Cu and dried. Thereafter, the obtained particles were impregnated with the sodium hydroxide solution so as to cause the molar ratio of OH/Cu to be 1.1 and dried. Thus, catalyst (E) was obtained.

The obtained support and catalyst were subjected to the same attrition resistance test and catalyst activity test as in Example 1. The results are given in Tables 1 and 2.

Example 6

Production of Solid Particles (Support)

700 g of active carbon powder prepared from petroleum pitch was mixed well with 1500 g of silica sol of 20% by weight in concentration (Cataloid S-20LE produced by Catalysts & Chemicals Industries Co., Ltd.) and pulverized. Subsequently, the mixture was spray dried to obtain fine spherical particles having an average particle size of 60 μm. These fine spherical particles were calcined at 600° C. in flowing nitrogen to obtain solid particles (f) having an average particle size of 60 μm. The properties of the particles (support) (f) are given in Table 1.

Production of Catalyst

The thus obtained solid particles were impregnated with the cupric chloride solution in an amount of 10% by weight in terms of Cu and dried. Thereafter, the obtained particles were impregnated with the sodium hydroxide solution so as to cause the molar ratio of OH/Cu to be 1.1 and dried. Thus, catalyst (F) was obtained.

The obtained support and catalyst were subjected to the same attrition resistance test and catalyst activity test as in Example 1. The results are given in Tables 1 and 2.

Comparative Example 1

Production of Silica Particles (Support)

5000 g of silica sol of 20% by weight in concentration (Cataloid S-20LE produced by Catalysts & Chemicals Industries Co., Ltd.) was spray dried, thereby fine spherical particles having an average size of 60 μm were obtained. The fine spherical particles were calcined at 500° C. in flowing nitrogen to obtain particles (g) having an average particle size of 60 μm. The properties of the particles (support) (g) are given in Table 1. The silica particles (g) had poor morphology and exhibited a high content of hollow or doughnut-shaped granules.

Production of Catalyst

The thus obtained silica particles were impregnated with the cupric chloride solution in an amount of 6% by weight in terms of Cu and dried. Thereafter, the obtained particles were impregnated with the sodium hydroxide solution so as to cause the molar ratio of OH/Cu to be 1.3 and dried. Thus, catalyst (G) was obtained.

The obtained support and catalyst were subjected to the same attrition resistance test and catalyst activity test as in Example 1. The results are given in Tables 1 and 2.

Comparative Example 2

Production of Catalyst

Active carbon from coconut husk of about 1 to 2 mm was pulverized and classified to obtain an active carbon (support) (h) having an average particle size of 0.1 mm. The thus obtained active carbon was impregnated with the cupric chloride solution in an amount of 10% by weight in terms of Cu and dried. Thereafter, the obtained active carbon was impregnated with the sodium hydroxide solution so as to cause the molar ratio of OH/Cu to be 1.3 and dried. Thus, catalyst (H) was obtained.

The obtained support and catalyst were subjected to the same attrition resistance test and catalyst activity test as in Example 1. The results are given in Tables 1 and 2.

Example 7

Production of Solid Particles (Support)

500 g of fused silica having a particle size of 0.7 μm was mixed with 750 g of silica sol of 40% by weight in concentration (Cataloid SI-80P having a particle size of 80 mμ, produced by Catalysts & Chemicals Industries Co., Ltd.) and 1000 g of silica sol of 20% by weight in concentration (Cataloid SI-550 having a particle size of 5 mμ, produced by Catalysts & Chemicals Industries Co., Ltd.). And then 97.4 g of an 85% phosphoric acid solution and 265 g of active carbon powder prepared from coal pitch were added thereto, mixed under agitation and pulverized by a wet pulverizer attritor to obtain a slurry of particles having a size of 2.7 μm. Subsequently, the slurry was spray dried to obtain fine spherical particles having an average size of 65 μm. The fine spherical particles were calcined at 600° C. in flowing nitrogen to obtain solid particles (support) (i). The results are given in Table 1.

Production of Catalyst

The thus obtained solid particles were impregnated with the cupric chloride solution in an amount of 10% by weight in terms of Cu and dried. Thereafter, the obtained solid particles were impregnated with the sodium hydroxide solution so as to cause the molar ratio of OH/Cu to be 1.2 and dried. Thus, catalyst (I) was obtained.

The obtained support and catalyst were subjected to the same attrition resistance test and catalyst activity test as in Example 1. The results are given in Tables 1 and 2.

Example 8

Production of Solid Particles (Support)

10 kg of an aqueous solution containing aluminum sulfate 2.5% by weight as $Al_2O_3$ was added to 10 kg of an aqueous solution containing sodium aluminate 5.0% by weight as $Al_2O_3$ to prepare an alumina hydrogel. This hydrogel was allowed to stand for 2 hr at 30° C. and washed to remove by-product. 3.0 kg of pure water was added to 12.9 kg of the resultant washed alumina hydrogel (7.0% by weight in concentration), and 226 g of active carbon powder prepared from coal pitch was added under vigorous agitation. The obtained slurry was passed through a dispersion mixer (manufactured by Asahi) and spray dried to obtain fine spherical particles having an average size of 63 μm. The fine spherical particles were calcined at 600° C. in flowing nitrogen to obtain solid particles (support) (j).

Production of Catalyst

The thus obtained solid particles were impregnated with the cupric chloride solution in an amount of 10% by weight in terms of Cu and dried. Thereafter, the obtained particles were impregnated with the sodium hydroxide solution so as to cause the ratio of OH/Cu to be 1.2 and dried. Thus, catalyst (J) was obtained.

The obtained support and catalyst were subjected to the same attrition resistance test and catalyst activity test as in Example 1. The results are given in Tables 1 and 2.

Example 9

Reaction in a Fluidized Bed Reactor

Reaction in a fluidized bed reactor was carried out using the above obtained catalyst (D).

1,300 ml of the catalyst (D) was charged in a stainless steel fluidized bed reactor of 53 mm in diameter. Then methanol, carbon monoxide and oxygen were fed through a gas distributor fitted at a lower part of the reactor at respective rate of 1.4 kg/hr, 2.74 Nm³/hr, and 0.091 Nm³/hr. The reaction was carried out at a temperature of 140° C. and a pressure of 8 Kg/cm²G to produce DMC. The performance of the catalyst at 5 hr from the initiation of the reaction is given in Table 2.

TABLE 1

Properties of Solid particles

| | Solid particles (support) | Type of active carbon | Ave. size (μm) | Content of active carbon (wt %) | Inorg. substance | Particle size of inorg. substance (μm) |
|---|---|---|---|---|---|---|
| Ex. 1 | a | coconut husk | 60 | 20 | silica | 0.016 |
| Ex. 2 | b | coconut husk | 60 | 5 | silica | 0.016 |
| Ex. 3 | c | sawdust | 70 | 10 | silica | 0.016 |
| Ex. 4 | d | coal | 60 | 30 | silica | 0.016 |
| Ex. 5 | e | petroleum pitch | 70 | 50 | silica | 0.016 |
| Ex. 6 | f | petroleum pitch | 60 | 70 | silica | 0.016 |
| Comp. Ex. 1 | g | (only silica) | 60 | 0 | silica | 0.016 |
| Comp. Ex. 2 | h | only active carbon | 100 | 100 | — | — |
| Ex. 7 | i | coal | 65 | 20 | silica | 0.7 0.08 0.005 |
| Ex. 8 | j | coal | 63 | 20 | alumina | — |

| | Other substance | Specific surface area (m²/g) | Pore vol. (ml/g) | Bulk density (g/ml) | Attrition resistance (wt %/15 hr) | Shape |
|---|---|---|---|---|---|---|
| Ex. 1 | | 405 | 0.36 | 0.65 | 3.5 | spherical |
| Ex. 2 | | 236 | 0.29 | 0.72 | 2.0 | spherical |
| Ex. 3 | | 301 | 0.33 | 0.68 | 3.0 | spherical |
| Ex. 4 | | 572 | 0.45 | 0.60 | 5.0 | spherical |
| Ex. 5 | | 719 | 0.60 | 0.55 | 6.8 | spherical |
| Ex. 6 | | 933 | 0.72 | 0.50 | 10 | spherical |
| Comp. Ex. 1 | | 150 | — | 0.67 | 2.0 | hollow, doughnut-shaped |
| Comp. Ex. 2 | | 1200 | — | 0.30 | 25 | pulverized |
| Ex. 7 | $P_2O_5$ | 285 | 0.25 | 0.90 | 1.0 | spherical |
| Ex. 8 | | 417 | 0.50 | 0.68 | 1.7 | spherical |

TABLE 2

| | Type of active carbon | Ave. size (μm) | Content of active carbon (wt %) |
|---|---|---|---|
| Ex. 1 | Catalyst A | coconut husk | 60 | 20 |
| Ex. 2 | Catalyst B | coconut husk | 60 | 5 |
| Ex. 3 | Catalyst C | sawdust | 70 | 10 |
| Ex. 4 | Catalyst D | coal | 60 | 30 |
| Ex. 5 | Catalyst E | petroleum pitch | 70 | 50 |
| Ex. 6 | Catalyst F | petroleum pitch | 60 | 70 |
| Comp. Ex. 1 | Catalyst G | only silica | 60 | 0 |
| Comp. Ex. 2 | Catalyst H | only active | 100 | 100 |

TABLE 2-continued

|  |  | carbon |  |  |
|---|---|---|---|---|
| Ex. 7 | Catalyst I | coal | 65 | 20 |
| Ex. 8 | Catalyst J | coal | 63 | 20 |
| Ex. 9 | Catalyst D | Coal | 60 | 30 |

| | Amount of supported Cu (wt %) | OH/Cu | Attrition resistance (wt %/15 hr) | DMC yield (%) |
|---|---|---|---|---|
| Ex. 1 | 6 | 1.3 | 4.1 | 12.5 |
| Ex. 2 | 6 | 1.3 | 2.0 | 1.8 |
| Ex. 3 | 10 | 1.5 | 3.3 | 3.7 |
| Ex. 4 | 10 | 1.3 | 5.0 | 12.1 |
| Ex. 5 | 10 | 1.1 | 7.0 | 12.3 |
| Ex. 6 | 10 | 1.1 | 10 | 12.5 |
| Comp. Ex. 1 | 6 | 1.3 | 2.0 | 0.5 |
| Comp. Ex. 2 | 10 | 1.3 | 25 | 11.7 |
| Ex. 7 | 10 | 1.2 | 1.1 | 12.6 |
| Ex. 8 | 10 | 1.2 | 1.9 | 10.0 |
| Ex. 9 | 10 | 1.3 | 5.0 | 12.4 |

$$\text{Content of active carbon (wt. \%)} = \frac{\text{wt. of active carbon}}{(\text{wt. of active carbon} + \text{wt. of inorg. substance} + \text{wt. of other substance})} \times 100$$

$$\text{Amount of Cu supported (wt \%)} = \frac{\text{wt. of Cu}}{(\text{wt. of CuCl}_2 + \text{wt. of solid particle})} \times 100$$

$$\text{DMC yield (\%)} = \frac{\text{mol. of methanol converted to DMC}}{\text{mol. of methanol fed}} \times 100$$

Example 10

Production of Catalyst 90 g of zinc acetate ($Zn(CH_3COO)_2 \cdot 2H_2O$) was dissolved in distilled water to obtain 270 ml of a zinc acetate solution.

100 g of solid-particles obtained in Example 1 were impregnated with 30 ml of the zinc acetate solution and dried at 100° C. This operation was repeated twice to obtain catalyst (K).

Vinyl Acetate Synthesizing Test

A vinyl acetate synthesizing test was conducted with the use of the above obtained catalyst (K).

10 ml of the catalyst was charged into a stainless steel pipe of 20 mm in inside diameter. Vinyl acetate was synthesized at atmospheric pressure and at a temperature of 200° C. by introducing acetylene and acetic acid at respective rates of 3 Nl/hr and 2.68 ml/hr.

The catalyst activity at 2 hr from the initiation of the reaction is given in Table 3.

Comparative Example 3

Production of Catalyst

Catalyst L was produced in the same manner as in Example 10 except that an active carbon prepared from petroleum pitch having an average particle size of 0.3 mm was employed in place of the solid particles. The results are given in Table 3.

TABLE 3

| | | Yield of vinyl acetate % |
|---|---|---|
| Example 10 | Catalyst K | 28 |
| Comparative Example 3 | Catalyst L | 20 |

What is claimed is:

1. Solid particles which comprise a substantially homogeneous mixture of an active carbon and an attrition-resistant inorganic substance and which have an average particle size of smaller than 300 μm, wherein the attrition-resistant inorganic substance comprises at least one metal oxide selected from the group consisting of silica, titania, zirconia, alumina and silica-alumina.

2. The solid particles as claimed in claim 1, wherein the average particle size ranges from 20 to 200 μm.

3. The solid particles as claimed in claim 1, wherein the active carbon is contained in an amount of 5 to 70% by weight.

4. The solid particles as claimed in claim 1, wherein the active carbon is contained in an amount of 5 to 50% by weight.

5. The solid particles as claimed in claim 1, which further comprise phosphorus and/or boron in an amount of 2 to 10% by weight as its oxide.

6. The solid particles as claimed in claim 1, which have a pore volume of 0.1 to 1.0 ml/g.

7. The solid particles as claimed in claim 6, which have a specific surface area of 100 to 1200 m²/g.

8. The solid particles as claimed in claim 7, which further comprise phosphorus and/or boron in an amount of 2 to 10% by weight as its oxide.

9. A process for producing solid particles which comprises the steps of:

spray drying a slurry containing an active carbon or a precursor thereof and an attrition-resistant inorganic substance or a precursor thereof so that particles having an average particle size of smaller than 300 μm are obtained, and calcining the particles, wherein the attrition resistant inorganic substance comprises at least one metal oxide selected from the group consisting of silica, titania, zirconia, alumina and silica-alumina.

10. The process as claimed in claim 9, wherein a phosphorus compound and/or a boron compound is included in the particles prior to the calcination.

11. The process as claimed in claim 9, wherein the solids in the slurry are subjected to a pulverizing or dispersing operation prior to the spray drying.

12. The process as claimed in claim 9, wherein the calcination of the particles is conducted at 400 to 800° C. in an atmosphere of inert gas.

13. A catalyst support comprising solid particles which comprise a substantially homogeneous mixture of an active carbon and an attrition-resistant inorganic substance and which have an average particle size of smaller than 300 μm, wherein the attrition resistant inorganic substance comprises at least one metal oxide selected from the group consisting of silica, titania, zirconia, alumina and silica-alumina.

14. A catalyst comprising solid particles which comprise a substantially homogeneous mixture of an active carbon and an attrition-resistant inorganic substance and which have an average particle size of smaller than 300 μm, wherein the attrition resistant inorganic substance comprises at least one metal oxide selected from the group consisting of silica, titania, zirconia, alumina and silica-alumina.

15. A catalyst comprising solid particles and a catalytic component supported thereon, wherein the solid particles comprise a substantially homogeneous mixture of an active carbon and an attrition-resistant inorganic substance and have an average particle size of smaller than 300 μm, wherein the attrition resistant inorganic substance comprises at least one metal oxide selected from the group consisting of silica, titania, zirconia, alumina and silica-alumina.

16. The catalyst as claimed in claim 15, which is a catalyst for producing a carbonic acid diester or vinyl acetate.

17. The catalyst as claimed in claim 16, which is a catalyst for producing a carbonic acid diester and comprises the solid particles and, supported thereon, a salt containing a metal and a halogen as the catalytic component.

18. The catalyst as claimed in claim 17, wherein the catalytic component supported on the solid particles comprises (i) a metal halide and (ii) an alkali metal compound and/or alkaline earth metal compound, (i) a metal halide and (iii) a tertiary organo-phosphorus compound having an aryl and/or alkyl group, or (i) a metal halide and (iv) an inorganic carbonate.

* * * * *

UNITED STATES PATENT AND TRADEMARK OFFICE
CERTIFICATE OF CORRECTION

PATENT NO. : 5,972,525
DATED : October 26, 1999
INVENTOR(S) : Kenji Mori et al.

It is certified that error appears in the above-identified patent and that said Letters Patent is hereby corrected as shown below:

Column 1 Line 19 "which include" should read --which includes--.

Column 1 Line 54 after "heat transfer," delete --a--.

Column 2 Line 47 between "is" and "suitable" delete period --.--.

Column 6 Line 45 between "compound" and "having" delete hyphen (-).

Column 7 Line 4 "dimethylcyclohexene" should read --dimethylcyclohexane--.

Column 7 Line 7 "cyclohexene" should read --cyclohexane--.

Column 9 Line 46 "(Cataloid s" should read --(Cataloid S--.

Column 13 Line 2 "m$\mu$" should read --$\mu$m--.

Column 13 Line 4 "5 m$\mu$" should read --5$\mu$m--.

Column 15 Line 43 between "solid" and "particles" delete hyphen (-).

UNITED STATES PATENT AND TRADEMARK OFFICE
CERTIFICATE OF CORRECTION

PATENT NO. : 5,972,525
DATED : October 26, 1999
INVENTOR(S) : Kenji Mori et al.

It is certified that error appears in the above-identified patent and that said Letters Patent is hereby corrected as shown below:

Column 17 Line 11, Claim 17, "in claim 16" should read --in claim 15--.

Signed and Sealed this

Eighth Day of August, 2000

Attest:

Attesting Officer

Q. TODD DICKINSON

Director of Patents and Trademarks